United States Patent
Gottschalk et al.

(12) 
(10) Patent No.: US 7,205,140 B2
(45) Date of Patent: Apr. 17, 2007

(54) NUCLEOTIDE SEQUENCE FOR CREATININE DEIMINASE AND METHOD OF USE

(75) Inventors: Ellen-Marie Gottschalk, Norten-Hardenberg (DE); Gerhard Gottschalk, Norten-Hardenberg (DE); Ruth Anne Schmitz-Streit, Gottingen (DE); Kai Thormann, Gottingen (DE)

(73) Assignee: CampusGen GmbH, Gottingen (DE)

( * ) Notice: Subject to any disclaimer, the term of this patent is extended or adjusted under 35 U.S.C. 154(b) by 450 days.

(21) Appl. No.: 10/689,564

(22) Filed: Oct. 20, 2003

(65) Prior Publication Data

US 2005/0084930 A1    Apr. 21, 2005

(51) Int. Cl.
C12N 9/78     (2006.01)
C12N 1/15     (2006.01)
C12N 1/21     (2006.01)
C12N 5/10     (2006.01)
C12N 15/63    (2006.01)
C07H 21/04    (2006.01)

(52) U.S. Cl. .............. 435/227; 435/252.3; 435/252.31; 435/252.33; 435/254.11; 435/320.1; 435/325; 435/348; 435/410; 536/23.2

(58) Field of Classification Search ............... 435/227, 435/252.3, 252.31, 252.33, 320.1, 325, 410; 536/23.2
See application file for complete search history.

(56) References Cited

FOREIGN PATENT DOCUMENTS

EP    1325958 A1 *  7/2003
JP    07143881      6/1995

OTHER PUBLICATIONS

Gottschalk et al., (1991) Creatinine deiminase (EC 3.5.4.21) from bacterium BN11: purification, properties and applicability in a serum/urine creatinine assay. *Clin Chim Acta.* 204(1-3): 223-38.

Farrow et al., (1995) Phylogenetic evidence that the gram-negative nonsporulating bacterium *Tissierella* (*Bacteroides*) *praeacuta* is a member of the *Clostridium* subphylum of the gram-positive bacteria and description of *Tissierella creatinini* sp. nov. *Int J Syst Bacteriol.* 45(3): 436-40.

Tanganelli et al., (1982) Enzymic assay of creatinine in serum and urine with creatinine iminohydrolase and glutamate dehydrogenase. *Clin Chem.* 28(7): 1461-4.

Austin and Huber, Genbank Database; accession S56903, publicly available Jun. 28, 1993.

* cited by examiner

*Primary Examiner*—Elizabeth Slobodyansky
(74) *Attorney, Agent, or Firm*—Barnes & Thornburg LLP; Alice O. Martin

(57) ABSTRACT

The present invention relates to the discovery of novel genes encoding a polypeptide having creatinine deiminase activity and methods of use. Also disclosed is a kit using the novel sequences for determining the concentration of creatinine in a sample.

20 Claims, 12 Drawing Sheets

FIG. 1

In the kidney:

L-Arginin + Glycin $\xrightarrow{\text{Transamidase}}$ Ornithine + Guanidinacetate

In the liver:

S-Adenosylmethionine + Guanidinacetate $\xrightarrow{\text{Guanidinoacetate-Methyltransferase}}$ Creatine + S-Adenosylhomocysteine

In muscle:

Creatine + ATP $\underset{\longleftarrow}{\xrightarrow{\text{Creatinekinase}}}$ Creatinephosphate + ADP Creatinephosphate $\longrightarrow$ Creatinine + Phosphate

FIG. 7

```
CTGGCATTAGTGTTATTGGCTATAGCAACAATTTTGTCAATAACTGATAAAAATACATTAACAAAAGAAAAACTGTAAGC     80
                                    rbs
TATTAACAATGCTAAATTTTTAAGGAGTGATTTTATGATGAAAAAGTTTATTAATGCAAAGATTTACAAGAACAATGAAG    160
                                       M  M  K  K  F  I  N  A  K  I  Y  K  N  N  E  A   16
                                       ———— cdi ————▶

CAACAGAAATTTTAGTAGAAGACGGTAAAATCAAAGAGATTGGTAATAACTTAGCAGACTGTAAAGAAGTAATTGATCTA    240
 T  E  I  L  V  E  D  G  K  I  K  E  I  G  N  N  L  A  D  C  K  E  V  I  D  L         42

GGCGGTAAAATGGTTACTCCACCTTATGTAGATCCTCACCTACATTTAGATTATGTGTATACATTGGCTGAACTTGGAAA    320
 G  G  K  M  V  T  P  P  Y  V  D  P  H  L  H  L  D  Y  V  Y  T  L  A  E  L  G  K     69

AACTGGTGCTGGCTCAGGAACTCTTTTTGAAGCTATTGAAATGTGGCCAGTATTTAAAAAGACTTTAACTGTAGAAAGCG    400
 T  G  A  G  S  G  T  L  F  E  A  I  E  M  W  P  V  F  K  K  T  L  T  V  E  S  V     96

TTAAAAAACTTGCTCTTAAGGGGGTTATGGATGAGGTTTCCCAAGGGGTACAACATATTCGTACACATATAGATGTAACT    480
 K  K  L  A  L  K  G  V  M  D  E  V  S  Q  G  V  Q  H  I  R  T  H  I  D  V  T        122

GATCCAAAATTCACAGGTCTAAAAGCTATGTTGGAAATGAAAGAAGAATTAAAGGACATAGTTGATATCCAAATAGTATC    560
 D  P  K  F  T  G  L  K  A  M  L  E  M  K  E  E  L  K  D  I  V  D  I  Q  I  V  S     149

ATTCCCACAACAAGGAATGTACACATATAAGGGTGGACGTGAATTAGTAGAAGAAGCACTTAAGATGGGTGCAGATGTTG    640
 F  P  Q  Q  G  M  Y  T  Y  K  G  G  R  E  L  V  E  E  A  L  K  M  G  A  D  V  V    176

TTGGAGGAATTCCGCATTATGAACCAGCTAGAGAATATGGTGAAATGTCTGTTAAAGCCACAGTTGAACTTGCTATGAAA    720
 G  G  I  P  H  Y  E  P  A  R  E  Y  G  E  M  S  V  K  A  T  V  E  L  A  M  K        202

TATGATAAGCTAATAGATGTTCACTGTGATGAGACAGATGATCCTCAAGCACGTTTTATTGAGCTATTAAATGCACTTGT    800
 Y  D  K  L  I  D  V  H  C  D  E  T  D  D  P  Q  A  R  F  I  E  L  L  N  A  L  V     229

TTATTTGGAAGGTTATGGTGCAAAAACTTCAGCTAGCCATACTTGTTCATTTGGTTCAGCAGATGATTCATATGCATATA    880
 Y  L  E  G  Y  G  A  K  T  S  A  S  H  T  C  S  F  G  S  A  D  D  S  Y  A  Y  R    256

GAATGATAGACTTATTCAAAAAGAGCAAGATAAACTTCATCTCTAATCCAACTGAAAATGCGTATCTACAAGGCCGTCAT    960
 M  I  D  L  F  K  K  S  K  I  N  F  I  S  N  P  T  E  N  A  Y  L  Q  G  R  H        282

GACACTTATCCAAAGCGTCGTGGATTGACTAGAGTTAAAGAATTTATGGAGCATGGTATTAATGTTGCATTTGCACAAGA   1040
 D  T  Y  P  K  R  R  G  L  T  R  V  K  E  F  M  E  H  G  I  N  V  A  F  A  Q  D    309

TTCAATAAACGATCCATGGTATCCAATGGGTAACGGAAATATGATGAATATACTTGACAATGGAATTCATTTAGCTCAAA   1120
 S  I  N  D  P  W  Y  P  M  G  N  G  N  M  M  N  I  L  D  N  G  I  H  L  A  Q  I    336

TAATGTCACCACAAGATATAGAAAAAGATTTAGATTTAATTACCTACAATGGTGCTCGTTGCCTAAATATCCAAGATAAA   1200
 M  S  P  Q  D  I  E  K  D  L  D  L  I  T  Y  N  G  A  R  C  L  N  I  Q  D  K        362

TATTTATTAGAAGTAGGTAAAGATTCAAACTTTATCGTTCTTAACGGAGACAGCCCATTCGATGTAATAAGAAACCGTGC   1280
 Y  L  L  E  V  G  K  D  S  N  F  I  V  L  N  G  D  S  P  F  D  V  I  R  N  R  A    389

TAATGTTCTTGCTTGTGTTAGAAAAGGAGAATTCTATTTAAGCAAAAACCAGTAGAATATGATGTAAAACTTGATTTAGG   1360
 N  V  L  A  C  V  R  K  G  E  F  Y  L  S  K  N  Q  *                                405
                                                  term              term
CGTAAAATATTAATATTTTAAAATAAATTCCAAATTAACCCCCCGGTGGTGTAATAAACTCCATCGGGGGGTTTTTTGTG   1440

TTCCAGTAGAAAATAAAAAAATGATATAAAAATTTAGTAGTTTGAAAAACTTAAATAAAGAAAGGGCGGATTTAGAATGA   1520

GTCAAAGAGACGTATTATATTCACCAGATGCAAAGTACAAAGATAATAAGGGTAAATATGGAATTGATTTAGG          1593
```

NUCLEOTIDE SEQUENCE FOR CREATININE DEIMINASE AND METHOD OF USE

BACKGROUND OF THE INVENTION

The present invention relates to the discovery of novel genes encoding a polypeptide having creatinine deiminase activity and methods of use. Also disclosed is a kit using the novel sequences for determining the concentration of creatinine in a sample.

The synthesis of creatinine is a multi-stage process that occurs in several different organs of the mammalian body, cf. FIG. 1 (Narayaman, S., Appleton, H. D. (1980). Clin. Chem. 26: 1119–1125). In the kidneys, ornithine and guanidine acetate are produced from the amino acids arginine and glycine, respectively. Once formed, ornithine and guanidine acetate travel from the kidneys, over the bloodstream, to the liver. Here, guanidine acetate is converted to creatine, and subsequently transported and distributed over the body, including to the musculature. In the muscular tissue, creatine can then undergo phosphorylation by creatine kinase (EC 2.7.3.2.) to create the high-energy molecule, creatine phosphate. Creatine phosphate functions as an important power supply for muscle tissue, by providing a ready source of reserve phosphate for the continuous regeneration of ATP during the fast bypass process of muscular energy production. During the recovery phase of muscle energy regeneration, creatine can be rapidly rephosphorylated to produce creatine phosphate. Typically, creatine phosphate is rapidly and continuously degraded to form free creatinine and inorganic phosphate.

The elimination of creatinine from the body is primarily performed by the kidneys, once the creatinine encounters the renal glomerular filtration apparatus. The elimination of creatinine takes place in a constant relationship with respect to overall muscle mass and body mass. When this relationship is compromised an increase of creatinine concentration in the plasma can result, indicating a possible disruption in muscle and/or kidney function.

Endogenously formed creatinine is typically neither reabsorbed nor excreted in the kidneys when creatinine metabolism is functioning properly. As such, measuring creatinine concentration in blood plasma could be a basis for diagnosing renal dysfunction. However, plasma creatinine concentration considered alone does not provide significant diagnostic sensitivity, thus its measurement is insufficient to evaluate kidney function, and in particular, the glomerular filtration rate of creatinine.

A preferred indicator for the status of the creatinine glomerular filtration rate, sufficient for clinical interests, is the measurement of endogenous creatinine clearance, whereby a determination of the creatinine concentration can be made in a sample of body fluid, including plasma and urine. Several clinical scenarios where determining the rate of endogenous creatinine clearance can be diagnostically useful include measuring a compromised glomerular filtration rate, discovering the presence of pathological urine components, hypertonia, ascertaining the status of chronic kidney patients, progress of hemodialysis treatment, metabolic disturbances, pregnancy, or medications producing potentially nephrotoxic metabolites.

Determining the creatinine concentration in the plasma and urine relies on several important chemical principles and procedures including colorimetric procedures for confirming and evaluating creatinine presence.

One common procedure used for detecting creatinine concentration in a sample is a colormetric reaction provided by the Jaffé method, whereby creatinine reacts with picric acid in an alkaline environment, to form a yellow-reddish complex (i.e. a Jankovski complex) (Jaffé, M. (1886) Z. Physiol. Chem. 10: 391–400), which is measured photometrically using a wavelength of 500–550 nm. One notable disadvantage of this procedure is its known nonspecificity, as numerous non-creatinine chromogenes, including bilirubin, glucose, ketone bodies, acetoacetate and pharmacons such as cephalosporine and metamizol can also form a Jankovski complex upon reacting with alkaline picrate (Soldin, S. J., Henderson, L., Hill, J. G. (1978). Clin. Chem. 26: 286–290; Kroll, M. H., Hagengruber, C., Elin, R. J. (1985). J. Biol. Chem. 115: 333–341; Swain, R. R, Briggs, S. L. (1977). Clin. Chem. 23: 1340–1342; Saah, A. J., Koch, T. R. Drusano, G. L. (1982). JAMA 247: 205).

To overcome the nonspecificity problems associated with the Jaffé method, scientists have made numerous attempts to improve the specificity in detecting the creatinine-picrate chromophore. For example, one attempt consisted of absorbing creatinine to Fullererde in order to accurately determine the creatinine concentration (Knoll, E., Stamm, D. (1970). J. Clin. Chem. Clin. Biochem. 8: 582–587; Knoll, E., Wisser, H. (1973). Z. Klin. Chem. Kin. Biochem. 11:411). Other efforts to determine creatinine concentration have included the use of an autoanalyzer of the "continuous flow generation", whereby a dialyzed sample is used for analysis. Such a sample was thought to reduce interference from external factors and competing substrates which could otherwise increase the error rate of the creatinine measurement (Popper, H., Mandel, E. Mayer, H. (1969). Biochem. Z. 291: 394; Scheuerbrandt, G., Helger, R. (1969). Aertztl. Lab. 15: 65).

A further known creatinine detection procedure includes reacting creatinine with o-nitrobenzaldehyde, whereby creatinine is degraded to methylguanidine and measured using the Sahaguchi reaction (Van Pilsum, J. F., Martin, R. P., Kito, E. Hess, J. (1956). J. Biol. Chem. 222: 225–236).

Another well known procedure for detecting creatinine involves reacting creatinine with 3,5-dinitrobenzoic acid and/or 3,5-dinitrobenzoylchloride to form a magenta-red complex, which is measured photometrically (Langley, W. D., Evens, M. (1936). J. Biol. Chem. 115: 333–341; Benedict, S. R., Behre, J. A. (1936). J. Biol. Chem. 114: 515–532; Sirota, J. H, Baldwin, D. S., Villareal, H. (1950). J. Clin. Invest. 29: 187–192).

None of these procedures shows improved specificity for ascertaining creatinine concentration when compared to the colorimetric measurement provided by the Jaffé method.

There are several different types of enzymatically-based procedures generally available to determine the creatinine concentration in a sample. In two of these procedures creatinine is converted in a first step to creatine using creatininase (EC 3.5.2.10).

One known procedure involves multiple enzymatic steps. For example, creatine is first converted to creatine phosphate via creatine kinase (EC 2.7.3.2.) to produce ADP, which in the presence of PEP and pyruvate kinase (EC 2.7.1.40) forms pyruvate and ATP, e.g., FIG. 2. The pyruvate is then converted to lactate in the presence of lactate dehydrogenase (EC 1.1.1.27) before a reaction with NADH. The degradation of pyruvate via NADH is measured by an extinction acceptance reaction at 340 nm, which can be directly correlated with the creatinine concentration in the sample.

Another procedure for creatinine detection in a sample includes the enzymatic conversion of creatinine by creatininase (EC 3.5.2.10.) to glycine, formaldehyde, and $H_2O_2$ (see FIG. 3).

This process requires two auxiliary reactions involving creatinase (EC 3.5.3.3.) and sarcosinoxidase (EC 1.5.3.1.). In a subsequent detection reaction, the increase in $H_2O_2$ formation is measured, upon the addition of peroxidase (EC 1.111.7.), via an extinction increase at 510 or 546 nm (Guder, W. G., Hoffman, G. E., Poppe, W. A., Siedel, J., Price, C. P. (1986). J. Chem. Clin. Biochem. 24: 889–902).

A further procedure for determining creatinine concentration is based on the creatinine deiminase (EC 3.5.4.21) catalyzed cleavage of creatinine to n-methylhydantoin and ammonia (Szulmajster, J. (1958). J. Bacteriol. 75: 633–639). The concentration of formed ammonia can be determined via a multilayer film technology using an indicator (Shirey, T. L. (1983). Clin. Biochem. 16: 147–152). Alternatively, the ammonia concentration can be determined as the ammonia reacts with α-ketoglutarate and NADPH/H+ in the presence of glutamate dehydrogenase to form glutamate, which can be measured photometrically via the extinction acceptance reaction at 340 and/or 365 nm (Lim, F. (1974). Clin. Chem. 20: 871; Tanganelli, E., Principe, L., Bassi, D., Cambiaghi, S., Murador, E. (1982). Clin. Chem. 28: 1461–1464; see FIG. 4).

The above-described enzymatic procedures for measuring creatinine concentration in a sample are generally not subject to the same interfering factors associated with the Jaffé method. However, these procedures fail to specifically measure only the creatinine concentration due to the presence of nonspecific substrates competing for creatinine deiminase in the catalytic reaction. For example, because both cytosine and all cytosine derivatives can effectively act as substrates for creatinine deiminase during the formation of creatinine, this necessarily results in an artificially high measurement of creatinine concentration in any particular sample where cytosine is present.

SUMMARY OF THE INVENTION

A novel gene encodes a protein having creatinine deiminase activity.

An isolated nucleic acid molecule encoding creatinine deiminase has the nucleic acid sequence set forth in SEQ ID NO:1 or a portion thereof. The disclosed molecules can be noncoding, (e.g. a probe, antisense, or ribozyme molecules) or can encode a functional creatinine deiminase polypeptide (e.g. a polypeptide which specifically modulates biological activity, by acting as either an agonist or antagonist of at least one bioactivity of the creatinine deiminase polypeptide). The claimed nucleic acid can hybridize with a nucleic acid sequence shown SEQ ID NO:1 or complement thereof under mildly stringent or highly stringent conditions.

The claimed nucleic acid molecule is a creatinine deiminase nucleic acid that is at least 50%, preferably at least 60%, more preferably at least 70%, and most preferably at least 80% homology to the nucleic acid sequence shown in SEQ ID NO:1 or a complement thereof. The nucleic acid sequence may exhibits at least 90%, specifically at least 95% or most specifically at least 98% homology to one or more ranges, preferably to the complete range of the nucleic acid shown as SEQ ID NO:1 or to the complement of the nucleic acid shown as SEQ ID NO:1.

A nucleic acid sequence as shown in SEQ ID NO:1, or a derivative or a complement thereof, encodes a protein having creatinine deiminase activity.

An isolated creatinine deiminase polypeptide, preferably substantially pure preparations, e.g. of plasma purified or recombinantly produced polypeptides can comprise a full length protein or can comprise smaller fragments corresponding to one or more particular motifs/domains, or fragments. Creatinine deiminase proteins have an amino acid sequence which is at least about 50%, preferably 60%, more preferably 70%, even more preferably 80%, more preferably 90%, or even more preferably 95% identical or homologous to an amino acid sequence of SEQ ID NO:2. Creatinine deiminase proteins may comprise an amino acid sequence which is at least about 97, 98, or 99% homologous or identical to an amino acid sequence of SEQ ID NO:2. The polypeptide has creatinine deiminase bioactivity, for example, it is capable of interacting with and/or cleaving a target peptide, such as creatinine.

The polypeptide is also encoded by a nucleic acid which hybridizes with the nucleic acid sequence represented in SEQ ID NO:1. The creatinine deiminase polypeptide comprises the amino acid sequence set forth in SEQ ID NO:2. Creatinine deiminase protein also includes within its scope modified proteins, e.g. proteins which are resistant to post-translational modification, for example, due to mutations which alter modification sites (such as tyrosine, threonine, serine or aspargine residues).

A purified or recombinant polypeptide, has the ability to modulate, e.g., mimic or antagonize, an activity of a wild-type creatinine deiminase protein, e.g., its ability to bind and/or cleave creatinine, or a peptide having a significant amino acid homology thereto. The polypeptide comprises an amino acid sequence identical or homologous to a sequence designated in SEQ ID NO:2.

Antibodies and antibody preparations are specifically reactive with an epitope of a creatinine deiminase protein.

A method for measuring the specific creatinine concentration in a sample, whereby interference with other substances, including cytosine and cytosine derivatives, is avoided, permits the rapid and specific determination of creatinine concentration for any sample or sample population. The method includes the steps of (a) forming a reaction mixture including: (i) a creatinine deiminase polypeptide and (ii) a creatinine deiminase substrate (e.g., a target peptide, such as creatinine); and (b) detecting the interaction of the creatinine deiminase polypeptide and the creatinine deiminase binding protein. The reaction mixture can be a cell-free protein preparation, e.g., a reconstituted protein mixture or a cell lysate, or it can be a recombinant cell including a heterologous nucleic acid recombinantly expressing the creatinine deiminase binding partner.

A kit for determining creatinine concentration in a sample, comprises a nucleic acid sequence of SEQ ID NO:1 or a fragment or a derivative thereof, or a host cell comprising said nucleotide sequence, or a polypeptide encoded for by said nucleotide sequence, and a reagent for determining the amount of ammonia.

Other aspects of the invention are described below or will be apparent to those skilled in the art in light of the present disclosure.

BRIEF DESCRIPTION OF THE DRAWINGS

FIG. 1: Biosynthesis of creatine and creatinine is a multistage process occurring in several different body organs.

FIG. 7: DNA and amino acid sequence of the creatinine deiminase subunit (cdi) from T. creatinini. The nucleotide sequence of a cDNA encoding creatinine deiminase gene (SEQ ID NO: 1) and the deduced amino acid sequence of the creatinine deiminase protein (SEQ ID NO 2) (Table 3).

DETAILED DESCRIPTION OF THE INVENTION

Figure 2:
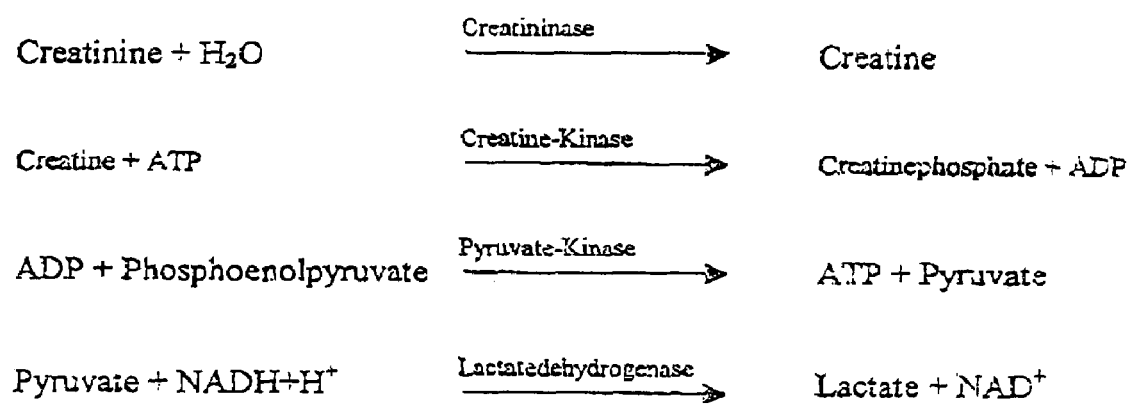
FIG. 2: Enzymatic regulation of creatinine with creatininase, creatine kinase, pyruvate kinase and lactate dehydrogenase. Creatinine undergoes catalysis by creatininase and creatine kinase coupled with pyruvate synthesis. In a subsequent indicator reaction, the pyruvate is converted to lactate via lactate dehydrogenase; extinction acceptance of an electron acceptor, including NADH or NADPH, is measured at 340 nm.

For convenience, the meaning of certain terms and phrases employed in the specification, examples, and claims are provided below.

A novel gene encodes a protein having creatinine deiminase activity. The creatinine deiminase gene transcript derived from Tissierella creatinini is represented as SEQ ID NO:1 and includes 5' and 3' untranslated regions and a 1218 base pair open reading frame encoding a 406 amino acid polypeptide as shown in SEQ ID NO:2.

A novel nucleic acid encoding creatinine deiminase, homologues thereof, and portions thereof, has a nucleic acid sequence having at least 50%, preferably at least 60%, more preferably at least 70% and most preferably at least 80% homology to the nucleic acid sequence shown in SEQ ID NO:1 or a complement thereof. The nucleic acid sequence may exhibit at least 90%, specifically at least 95% or most specifically at least 98% homology to one or more ranges, to the complete range of the nucleic acid sequence represented in SEQ ID NO:1, or to the complement of the nucleic acid shown in SEQ ID NO:1.

Isolated nucleic acids comprise a nucleotide sequence encoding creatinine deiminase polypeptides, variants and/or equivalents of such nucleic acids according to the invention, whereby the sequence codes for a polypeptide that does not deaminate cytosine.

As used herein, the term "nucleic acid" refers to polynucleotides such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides.

The term "nucleic acid sequence coding for a protein or polypeptide having creatinine deiminase activity" refers to a general form of successive nucleotide bases, which determines directly or over a complementary set of nucleotide bases, an amino acid sequence of a protein or a polypeptide having creatinine deiminase activity.

The term "creatinine deiminase activity" means enzymatic activity, including the activity whereby creatinine is converted to n-methylhydantoin and ammonia.

The term "equivalent" is understood to include nucleotide sequences encoding functionally equivalent creatinine deiminase polypeptides or functionally equivalent peptides having an activity of a creatinine deiminase protein as described herein. Equivalent nucleotide sequences will include sequences that differ by one or more nucleotide substitution, addition or deletion, and will, therefore, include sequences that differ from the nucleotide sequence of the creatinine deiminase gene shown in SEQ ID NO:1 due to the degeneracy of the genetic code. Nucleic acids having a sequence that differs from the nucleotide sequence shown in SEQ ID NO:1 or a complement thereof due to degeneracy in the genetic code is also within the scope of the invention.

Such nucleic acids encode functionally equivalent peptides (i.e., a peptide having a biological activity of a creatinine deiminase polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a creatinine deiminase polypeptide.

A nucleic acid sequence is for deoxyribonucleic (DNA) or ribonucleic (RNA). A nucleic acid can be isolated from any naturally occurring environment or synthesized in vitro. The term "isolated" as used herein with respect to nucleic acids, such as DNA or RNA, refers to molecules separated from other DNAs, or RNAs, respectively, which are present in the natural source of the macromolecule. Nucleic acid sequences include genomic DNA, cDNA, recombinant DNA, and other chemically synthesized molecules. The nucleic acid sequence may be derived from *Tissierella creatinin*, be a recombinant nucleic acid sequences and can be single stranded, double stranded or linear or covalent or represented as a closed circle molecule.

A nucleic acid sequence, which is complementary to a nucleic acid sequence codes for a protein or polypeptide having creatinine deiminase activity. The term "nucleotide sequence complementary to the nucleotide sequence set forth in SEQ ID NO:1" refers to the nucleotide sequence of the complementary strand of a nucleic acid strand having SEQ ID NO:1.

The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO:1 refers to the complementary strand of the strand having SEQ ID NO:1 or to any nucleic acid having the nucleotide sequence of the complementary strand of SEQ ID NO:1. When referring to a single stranded nucleic acid having the nucleotide sequence SEQ ID NO:1, the complement of this nucleic acid is a nucleic acid having a nucleotide sequence which is complementary to that of SEQ ID NO:1. The nucleotide sequences and complementary sequences thereof are given in the 5' to 3' direction.

The term "derivative" of a nucleic acid sequence means an individual or multiple nucleotide substitution, deletion and/or addition in the nucleic acid sequence. Furthermore, the term "derivative" also refers to a chemical derivative of a nucleic acid sequence at a nucleotide base, including a derivative in the sugar or phosphate moieties. The term "derivative" also refers to nucleic acid sequences containing naturally occurring nucleotides and nucleotide analogues.

Nnucleic acid sequences can be provided alone or in combination with other nucleic acid sequences, especially heterologous nucleic acid sequences. The nucleic acid sequence is provided in connection with expression control sequences, said expression control sequences can be homologous or heterologous with respect to the inventive novel acid sequence.

A recombinant DNA molecule codes for a protein or polypeptide having creatinine deiminase activity, or a complementary nucleic acid sequence thereof. The recombinant DNA molecule is a vector or a plasmid, if necessary with a promoter, which controls the expression of the nucleic acid sequence according to invention.

The term "vector" refers to a nucleic acid molecule, either eukaryotic or prokaryotic in origin, capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors". In general, expression vectors used in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "expression control sequence" means that the subject nucleic acids can be operably linked to a transcriptional regulatory sequence, e.g., at least one of a transcriptional promoter (e.g., for constitutive expression or inducible expression) or transcriptional enhancer sequence. Such regulatory sequences in conjunction with a creatinine deiminase nucleic acid molecule can provide a useful vector for gene expression. As used herein, the term "promoter" means a DNA sequence that regulates expression of a selected DNA sequence operably linked to the promoter, and which controls expression of the selected DNA sequence in cells.

Host cells are transfected with expression vectors whether prokaryotic or eukaryotic. In vitro (e.g. cell culture) methods for producing creatinine deiminase proteins employ expression vectors. As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a creatinine deiminase polypeptide or, in the case of antisense expression from the transferred gene, the expression of a naturally-occurring form of the creatinine deiminase polypeptide is disrupted.

Host cells contain a nucleic acid sequence. The term "host cell" describes a cell having a transformable or transfectable exogenous nucleic acid sequence. Host cells can be prokaryotic or eukaryotic cells in origin, including yeast cells, insect cells, plant cells and mammalian cells. Preferential cells include the prokaryotic Escherichia coli or Bacillus subtilis. The nucleic acid sequences disclosed herein can be present in the host cell in one or multiple copies.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "expression" means the production of RNA or of RNA and protein, or even a partial expression of nucleic acid sequences. Moreover, expression can take place in a transient or stable manner.

In a further embodiment, the invention describes an oligonucleotide that is suitable as a genetic probe, which hybridizes to a nucleic acid sequence according to invention. "Antisense" molecules can also be used. Nucleic acid molecules in the form of oligonucleotide primers or competent samples, which hybridize with a nucleic acid sequence according to invention or parts of it, in particular with the nucleic acid sequence represented in SEQ ID NO:1, can be suitable for identifying nucleic acid sequences, which are homologous to the nucleic acid sequence according to invention and coding for a protein having creatinine deiminase activity. Additionally, PCR amplification, Southern and Northern hybridizing can be used for locating homologous nucleic acid sequences. Hybridization can occur under low, preferably under medium, or most preferably under high stringency conditions. The term "stringency conditions" according to the invention describes those conditions typically used to achieve specific hybridization between polynucleotides. "Antisense" molecules can be used for the modulation, specifically inhibiting, the expression of a nucleic acid sequence according to invention. As used herein, "antisense" refers to a molecule or its derivatives which specifically hybridize (e.g., bind) under cellular conditions, with the cellular mRNA and/or genomic DNA encoding one or more of the subject creatinine deiminase proteins so as to inhibit expression of that protein, e.g., by inhibiting transcription and/or translation. The binding may be by conventional base pair complementarity, or, for example, in the case of binding to DNA duplexes, through specific interactions in the major groove of the double helix.

An "antisense molecule" refers to a construct, which contains a nucleic acid sequence according to the invention or a derivative thereof, in reverse orientation with respect to the promoter. An antisense construct can be delivered, for example, as an expression plasmid which, when transcribed in the cell, produces RNA which is complementary to at least a unique portion of the cellular mRNA which encodes a creatinine deiminase protein.

Alternatively, the antisense construct is an oligonucleotide probe which, when introduced into the cell, causes inhibition of expression by hybridizing with the mRNA and/or genomic sequences of a creatinine deiminase gene. Such oligonucleotide probes include modified oligonucleotides which are resistant to endogenous nucleases, e.g., exonucleases and/or endonucleases, and are therefore stable in vivo. For example, an antisense construct is an oligonucleotide according to invention having a length of 6 to 50 nucleotides, preferably 10 to 30 nucleotides and most preferably 15 to 20 nucleotides. Such antisense construct is preferably completely or partially complementary to the subject nucleic acid sequence.

An isolated polypeptide having creatinine deiminase activity, is isolated from, or otherwise substantially free of, other cellular proteins.

Creatinine deiminase proteins have an amino acid sequence which is at least about 50%, preferably 60%, more preferably 70%, even more preferably 80%, more preferably 90%, or even more preferably 95% identical or homologous to an amino acid sequence of SEQ ID NO:2. Creatinine deiminase proteins comprise an amino acid sequence which is at least about 97, 98, or 99% homologous or identical to an amino acid sequence of SEQ ID NO:2. Such proteins can be recombinant proteins, and can be, e.g., produced in vitro from nucleic acids comprising a nucleotide sequence set forth in SEQ ID NO:1, or homologues thereof. For example, recombinant polypeptides can be encoded by a nucleic acid, which is at least 90% homologous and more preferably 95% homologous and most preferably 98% homologous with a nucleotide sequence set forth in SEQ ID NO:1. Polypeptides are encoded by a nucleic acid that is at least about 98–99% homologous with the sequence of SEQ ID NO:1.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

"Derivatives" of the protein or polypeptide according to invention refers to individual or multiple substitutions, deletions and/or additions of any molecules, which are associated with the enzyme, including, for example, carbohydrates, lipids and/or proteins or polypeptides. Furthermore the term "derivative" extends also to all functional chemical equivalents of the proteins or polypeptide according to the present invention.

Amino acid deletion and insertion variants are characterized by removing or adding one or more amino acids from the protein sequence, respectively. Amino acid substitution variants generally refer to a sequence whereby one amino acid in the protein sequence is removed and replaced by another. These modifications may occur in positions which are not conserved in homologous proteins or polypeptides. A modification occurs whereby one amino acid is replaced by another having similar characteristics hydrophobicity, hydrophilicity, electronegativity, and spacing of the side chain, i.e. a conservative substitution.

A conservative substitution describes the exchange of one amino acid for another. The following substitution classes are exemplary conservative substitutions: a small aliphatic, non-polar or easy-polar substitution includes the interchangeability of alanine, serine, threonine, proline and glycine; a negatively charged substitutions includes the interchangeability of asparagine, aspartate, glutamine, glutamate; a positively charged substitution includes the interchangeability of histidine, arginine and lysine; and a large aliphatic, non-polar substitution includes the interchangeability of methionine, leucine, valine, isoleucine and cystine; and a large aromatic substitution includes the interchangeability of phenylalanine, tyrosine, and tryptophan.

The amino acid variants described above can easily prepared using well-known peptide synthesis techniques including "Solvent Phase Synthesis" (Merrifield, R. B., Stewart J. M. (1965), Nature 207: 522–523) or by recombinant DNA manipulation and related procedures. Techniques introducing substitution mutations into predetermined locations into a DNA that have a known or partly known sequence are available and use mutagens such as, for example, M13-Mutagenese. The process of preparing proteins from DNA sequences, including those with substitutions, insertions, or deletions is described by Sambrook et al. (Sambrook, J., Fritsch, E. F., Maniatis, T. (1989), Cold Spring Harbour Laboratory).

A procedure is presented for making a polypeptide having creatinine deiminase bioactivity, whereby a nucleic acid sequence is expressed in a host cell and the resulting polypeptide is subsequently isolated. The term "isolated" is also used herein to refer to polypeptides which are isolated from other cellular proteins and is meant to encompass both purified and recombinant polypeptides. The isolation of a polypeptide takes place via ammonium sulphate precipitation and chromatography utilizing sepharose columns, including Phenyl-sepharose and DEAE-Sepharose CL6B.

The terms "protein", "polypeptide" and "peptide" are used interchangeably herein when referring to a gene product. The term "recombinant protein" refers to a polypeptide which is produced by recombinant DNA techniques, wherein generally, DNA encoding a creatinine deiminase polypeptide is inserted into a suitable expression vector which is in turn used to transform a host cell to produce the heterologous protein. Moreover, the phrase "derived from", with respect to a recombinant creatinine deiminase gene, is meant to include within the meaning of "recombinant protein" those proteins having an amino acid sequence of a native creatinine deiminase polypeptide, or an amino acid sequence similar thereto which is generated by mutations including substitutions and deletions (including truncation) of a naturally occurring form of the polypeptide.

A polypeptide has creatinine deiminase bioactivity, for example, and it is capable of interacting with and/or cleaving the target peptide, such as creatinine. "Biological activity" or "bioactivity" or "activity" or "biological function", which are used interchangeably, for the purposes herein means an effector or antigenic function that is directly or indirectly performed by a creatinine deiminase polypeptide (whether in its native or denatured conformation), or by any subsequence thereof.

A procedure for determining the creatinine concentration in a sample using the subject polypeptide includes a reaction mixture containing a creatinine deiminase protein and a substrate. A suitable substrate is creatinine or portions thereof sufficient for interacting with the creatinine deiminase protein.

The sample may be a body fluid, including plasma, serum or urine. Determining the creatinine content in a body fluid sample can provide useful information about the renal glomerular filtration rate, including the volume of liquid filtered per unit time. For example, an irregularity observed in the creatinine levels of a body fluid sample can be a basis for diagnosing muscle or renal illness, including muscle tissue breakdown or nephritis, respectively.

The sample may come into contact with a creatinine deiminase polypeptide, and the amount of formed ammonia is subsequently determined. Determining ammonia concentration may occur after reacting the ammonia with glutamate dehydrogenase in presence of α-ketoglutarate and an electron acceptor, such as NADH or NADPH. In this extinction acceptance reaction, the consumption of the electron receptor is measured, e.g. by photometric measurement at 340 and/or 365 nm.

A technique for specifically measuring the creatinine concentration of a sample includes a simple indicator reaction step is provided, whereby no complicated auxiliary measurement reactions are necessary. As illustrated by Table 1, the creatinine deiminase according to the present invention exhibits a significant preference for the creatinine substrate, without any interference from, for example, cytosine at a concentration up to 2000 mg/ml. Therefore, the subject creatinine deiminase polypeptide specifically and preferentially interacts with creatinine also in presence of other substrates with high specificity, without undue interference from other molecules which would otherwise compromise the accuracy of the measured value for the creatinine concentration in the sample.

TABLE 1

Interference studies using the purified heterologously expressed creatinine deiminase from *Tissierella creatinini* with different compounds found in blood serum. In each case, these compounds were added to a reaction mixture and the enzyme activity of the creatinine deiminase was determined. For each compound tested, no interference was detected at the indicated concentration.

| Compound/Solution | Maximum concentration without interference (mg/l) |
|---|---|
| Acetoacetate/$H_2O$ dist. | 7.8 |
| Acetone/$H_2O$ dist. | 2000 |
| Acetic acid/$H_2O$ dist. | 200 |
| Bilirubin | 210 |
| Captopril | 83 |
| Ceficitin/$H_2O$ dist. | 860 |
| Creatine/$H_2O$ dist. | 2000 |
| Cytosine | 2000 |
| Epinephrine/$H_2O$ dist. | 0.05 |
| Etomedac | 666 |
| Fluoroblastin | 33 |
| 5-Fluorocytosine $H_2O$ dist. (Ancotil) | 1000 |
| Fuoresemide | 4433 |
| Glucose | 1100 |
| Hemoglobin (hemolyzed serum) | 0 |
| Histidine/aqua bidest | 2250 |
| IgM | 20,000 |
| α-Methyl-Dopa/ $H_2O$ dist. | 107 |
| Neogama D novo | 666 |
| Nitrofurantoin/$H_2O$ dist. | 200 |
| Norepinephrine/$H_2O$ dist. | 1.5 |
| Oxalic acid/$H_2O$ dist. | 400 |
| Predni H Tablinen (Prednisolone) | 278 |
| Pyruvate/$H_2O$ dist. | 5.9 |
| Salazosulphapyridine/Methanol | 550 |
| Sulphamethoxazole/Acetone | 500 |
| Trimethoprime/Methanol | 46 |
| Vancomycin | 288 |

A kit for determining the creatinine concentration in a sample includes a nucleic acid sequence according to invention, coding for a polypeptide having creatinine deiminase activity, or a host cell comprising a subject nucleic acid or polypeptide having creatinine deiminase activity. Other reagents can be included in the kit that are useful for measuring the creatinine level in a sample, including but not limiting to, free ammonia. Collectively, these components offer a specific and accurate determination of creatinine concentration present in a particular sample.

EXAMPLES

Example 1

Cloning of the Creatinine Deiminase Gene ("cdi Gene") from *T. creatinini*

Purification of the Creatinine Deiminase from *Tissierella creatinini*

The culturing of *Tissierella creatinini* was carried out in Hungate tubes (Bellco Glass Inc., Vineland, USA) and incubated at 37° C. in an anaerobic medium, according to Bryant (Bryant, M. P. (1972), Am. J. Clin. Nutr. 25:1324–1328) and further according to a modified Hungate technique (Hungate, R. E. (1969). In: Norris, J. R. Ribbons, D. W. (Hrsg.) Methods in Microbiology 3B: 117–132. Academic Press, London). After adjusting the pH value of the medium using $N_2/CO_2$ (80/20% (v/v)), the tubes were then autoclaved at 121° C. for 20–30 min. Before inoculation, a separately autoclaved reducing agent (L-cysteine, 5% (w/v)) was added to the cell mixture.

The disruption of the cellular integrity was performed using a French press (SLM Instrument Company, Urbana, USA) having a pressure in a range from 62 to 103 Mpa. Cellular debris and undisrupted cells were removed by centrifugation (10000–12000×g, 10 min, 4° C.). The cell-free extract was then referred to as the raw extract.

Creatinine deiminase derived from *Tissierella creatinini* (Gauglitz, U. (1988), Thesis University of Goettingen), having an initial mass of 15 g of *T. creatinini* cells, was purified to apparent homogeneity according to known procedures (Gottschalk, E. M., Hippe, H., Patzke, F. (1991). Clin. Chim. Acta 204: 223–238).

Sequencing of the Purified Creatinine Deiminase Polypeptide

The purified creatinine deiminase was denatured via Endoproteinase Glu C from *Staphylococcus aureus* V8 according to the method of Cleveland et al. (Cleveland, D. W., Fischer, S. G., Kirschner, M. W., Laemmli, U. K. (1977). J. Biol. Chem. 252: 1102–1106) and separated on an SDS-polyacrylamide gel. The fragments were then transferred onto a PVDF membrane (Immobilon-P transfer membrane, Millipore Corporation, USA) using a Semi-Dry Fast-Blot device (Multiphor II Nova Blot, Inc., Pharmacia LKB GmbH, Freiburg). The N-terminus of the creatinine deiminase and an internal peptide (28 kDa) were then sequenced using Procise 491 protein sequencers (Applied Biosystems, USA).

Isolation of Chromosomal DNA from *T. creatinini*

Isolation of chromosomal DNA from *T. creatinini* was performed according to a modified method described by Betram and Dürre (Bertram, J. Dürre, P. (1989) Arch. Microbiol. 151: 551–557).

Production and Hybridizing of a Specific Probe Against the Creatinine Deiminase Coding Gene (cdi Gene)

Figure 5:
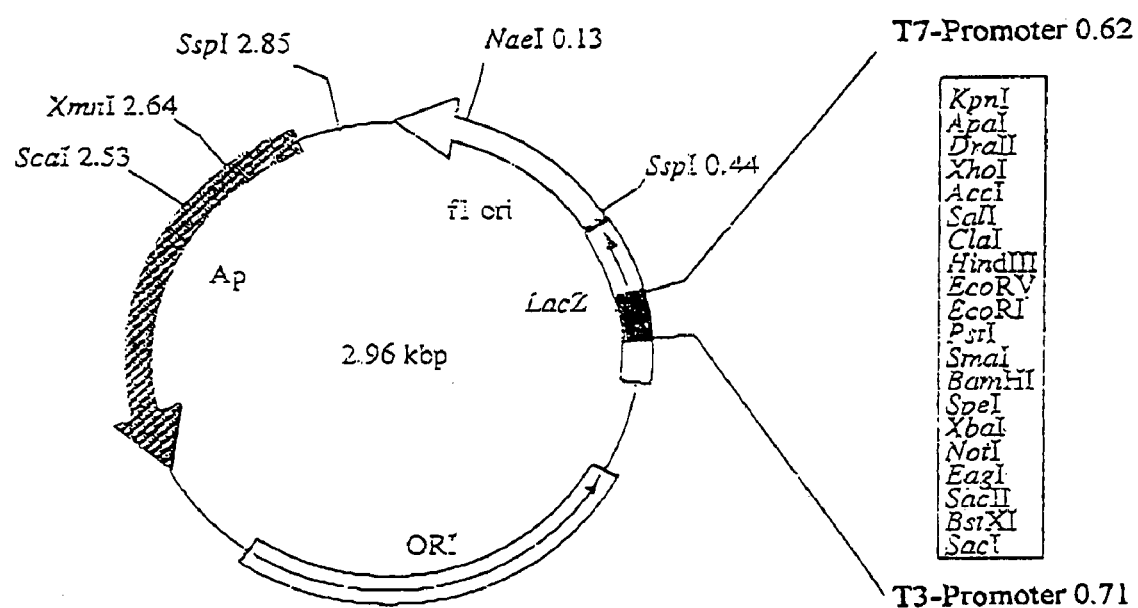
FIG. 5: Schematic representation of the pBluescriptSK+ vector. Multiple restriction sites are shown. Abbreviations: f1 ori: Phage f1 Replication origin; Ap: Ampicillin resistance; ORI: replication origin for E. coli; LacZ: α-complementation fragment of the β-galactosidase; kbp: kilobase pair, size.

Heterologous oligonucleotides were prepared using the N-terminal amino acid sequences of the N-terminal domain for the creatinine deiminase gene. Using these oligonucleotide and chromosomal DNA derived from *T. creatinini* as primers for a subsequent polymerase nuclear chain reaction (PCR), a 600 bp specific probe was isolated from the cdi gene. The probe was labelled with the nonradioactive DNA labelling kit available from Boehringer Mannheim (Mannheim, Germany) and then used in a Southern blotting procedure to identify the presence of a cdi gene sequence. The Southern blots were carried out according to the method of Sanbrook et al. 1989 (supra) and Ausubel et al. 1987 (Ausubel, F., Brent, R., Kingston, R. E., Moore, D. D., Seidmann, J. G., Smith, J. A. Struhl, K. (1987). John Wiley and Sons, New York). A single 4.5 kbp large HindIII restriction DNA fragment was identified, which specifically hybridized with the 600 bp probe containing sequences derived from the cdi gene. The cdi gene derived from *T. creatinini* was cloned into the pKS+ vector (see FIG. 5) using known "Shotgun Cloning" techniques. For this purpose, the HindIII restriction fragment was ligated into a chromosomal *T. creatinini* DNA using a HindIII linearized pBluescript SK+ (pSK+) vector (Stratagene, Heidelberg; Ap$^r$, lac POZ') and transformed in *Escherichia coli* DH5α (Hanahan, D. (1983). J. Mol. Biol. 166: 557–580; genotype: F-, lacZDM15, recA1, hsdR17, supE44, Δ(lacZYA, argF). The cultivation of *E. coli* took place as described in Luria Bertani (LB) medium with the appropriate medium additives (Sambrook et al., 1989, supra).

Figure 6:
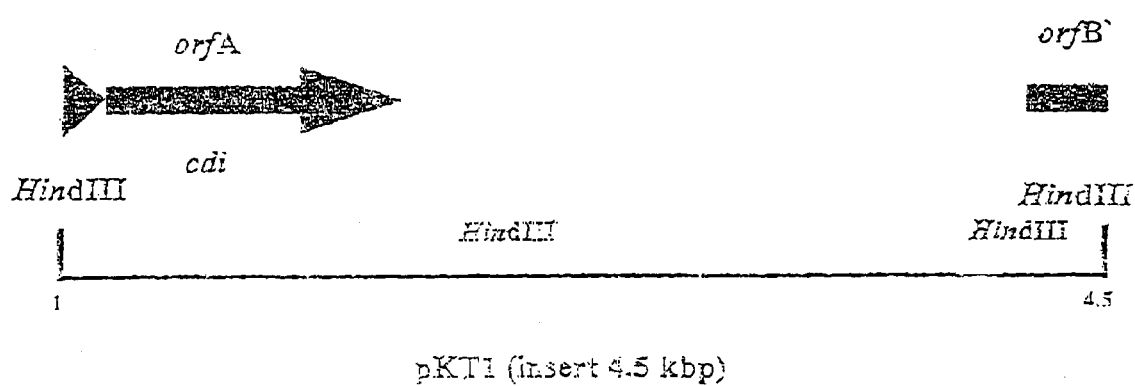
FIG. 6: Schematic representation of the recombinant vector pKT1. The cloned fragment with flanking HindIII interfaces is shown. Abbreviations: cdi: the orientation and reading frame direction of the creatinine deiminase subunit; kbp: kilobase pair, size.

The resulting clones were analyzed via colony hybridization using the labelled 600 bp probe to detect the presence of the cdi gene. The colony hybridization was performed according to those methods described by Sambrook et al. 1989 (supra). The detection of the DIG-labelled probe was performed according to manufacturer specifications (Boehringer, Mannheim) using the CSPD detection solution. A positive clone was identified, exhibiting a 4.5 kbp large fragment insert. This recombinant plasmid was designated as pKT1 (4.5 KB HindIII DNA fragment of *T. creatinini* in pSK+). By creating a restriction map for 4.5 kbp fragment, the location of the complete cdi gene was ascertained (see FIG. 6).

Example 2

Sequencing and Analysis of the cdi Gene from *T. creatinini*

The sequence of the cdi gene from the 4.5 kbp insert from the pKT1 plasmid was determined on both strands using the known "primers walking" method (Strauss, E. C., Kobori, J. A., Siu, G., Hood, L. E. (1986). Anal. Biochem. 154: 353–360). The DNA sequencing was performed using an Automated Laser Fluorescent Sequencer (ALF) and a PC installed with the software "ALF Manager v. 2.6" (Pharmacia LKB, Freiburg). For the sequencing reactions, the "Auto-READ Sequencing Kit" (Pharmacia LKB, Freiburg) was used. Sequencing was performed using the fluorescence tagged universal primers provided by the sequencing kit and/or using the sequence-derived fluorescence tagged primers (MWG Biotech GmbH (Ebersberg)).

Analysis of the sequence data was performed using the program DNA STRIDER, v. 1.2 (Marck, C. (1988). Nucl. Acids Res. 16: 1829–1836) on a Macintosh computer (Apple Computer, Cupertino, USA). Sizeable sequence analyses were performed with the assistance of the "Wisconsin GCG Sequence Analysis Software Package" v. 8 (Genetics Computer Group, University of Wisconsin Biotechnology Center, Madison, USA) on a computer having a UNIX based operating system. For sequence comparisons, the gene and protein data banks EMBL, GenBank and SwissProt were consulted. The cdi gene exhibited a length of 1218 bp, coding for 406 amino acids, and a calculated molecular weight of 47.5 kDa. This molecular mass measurement (47.5 kDa) agrees substantially with the value determined for the isolation of the purified protein under denaturing conditions using gel electrophoresis. The complete sequence of the cdi gene, including the derived amino acid sequence, is depicted in FIG. 7.

The amino acid sequence for creatinine deiminase derived from *T. creatinini* showed a high homology to the cytosine deaminase (codA) of *E. Coli*, which is able to metabolize creatinine.

Downstream of the cdi gene is the N-terminal range of an open reading frame (orf), comprising an amino acid sequence having a high homology to the n-carbamoylsarcosine-amidohydrolase of *Arthrobacter* sp. (see FIG. 6). Thus, the orf for N-terminal part of the *T. creatinini* contains a sequence for n-carbamoylsarcosine-amidohydrolase, the third enzyme of the creatinine metabolic pathway.

Example 3

Figure 8:
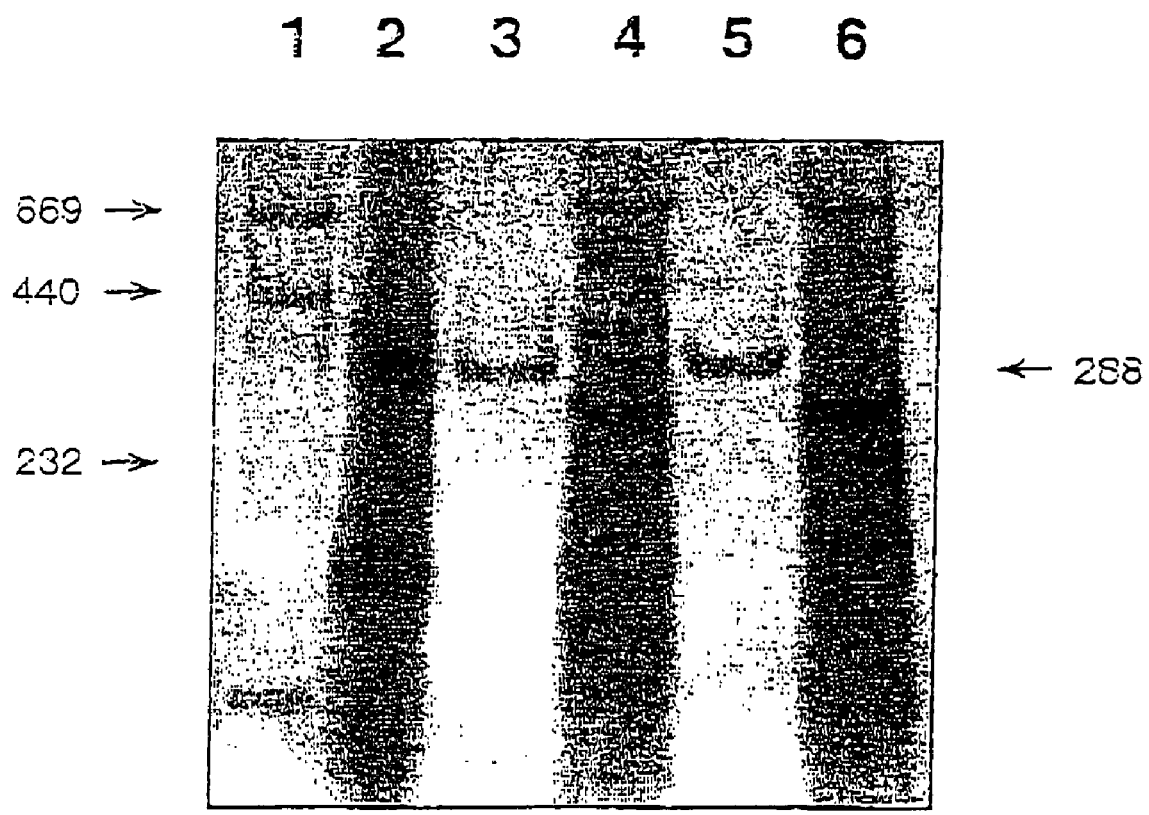
FIG. 8: Gel electrophoresis under native conditions for the expression identity of the creatinine deiminase from T. creatinini after heterologous expression in E. coli. The size of the bands indicated by the arrows is represented in kDa. Lane 1: protein standard (thyroglobulin, ferritin, catalase, lactate dehydrogenase, albumin); Lane 2: raw extract of Tissierella creatinini (approx. 25 µg); Lane 3 and 5: purified creatinine deiminase (5 µg); Lane 4: raw extract of E. coli DH5αpKT1 (approx. 15 µg); lane 6: raw extract of E. coli DH5α/pBluescript (approx. 15 µg).

Heterologous Expression and Purification of an Active Creatinine Deiminase from T. creatinini in E. coli The heterologous expression of an active creatinine deiminase derived from T. creatinini in E. coli (from the recombinant cell extract) was analyzed using gel electrophoresis (FIG. 8) and by determining the enzymatic activity in the cell-free raw extracts. Gel electrophoresis showed that in the case of E. coli DH5α/pKT1 (contrary to that seen for E. coli DH5α/pKS+) an additional and clearly viewable band of approximately 300 kDa (see FIG. 8, lane 4 and lane 6). Additionally, a band for the purified creatinine deiminase appeared at this same distance of 300 kDa (see FIG. 8, lanes 3 and 5), and likewise a similar band appeared in the raw extract of T. creatinini (FIG. 8, lane 2). The predicted size for creatinine deiminase (300 kDa) is well within range of the known value (288 kDa) as determined by Gottschalk et al. 1991 (supra). The specific activity of the recombinant creatinine deiminase in the cell-free extract was determined to be about 10.2 U/mg.

Heterologous sequences expressing creatinine deiminase (EC 3.5.4.21), as derived from T. creatinini, were also purified according to methods described by Gottschalk et al. 1991 (supra). The creatinine deiminase protein was purified from 5 g of cells using ammonium sulphate precipitation and chromatography to apparent homogeneity using phenylsepharose and DEAE-Sepharose CL6B (see FIG. 9). The specific activity of the purified recombinant enzyme was determined to be 1423 U/mg (see Table 2). The enzyme was suspended in a potassium phosphate buffer (KPP; pH 7.65, 50% Glycerin) and stored at −20° C. in. The purification steps are described as follows:

Step 1: Preparation of Cell-Free Extracts from T. creatinini

A 5 g cell mass was resuspended in a buffer containing 0.05 mol/l potassium phosphate, pH 7.65, 0.1 mg/ml ribonuclease, and 0.1 mg/ml deoxyribonuclease before being subjected three separate times to a French press at a pressure of 120 MPa to disrupt membrane integrity. Cellular debris was then removed by centrifugation (50000×g, 10 min and 4° C.). The cell-free supernatant was referred to as raw extract.

Step 2: Ammonium Sulphate Precipitation

The raw extract (14.7 ml) was adjusted to a 0.65 saturation using ammonium sulphate at 0° C. and centrifuged (50000×g, 15 min, 4° C.). The resulting precipitate, containing the enzyme, was then resuspended into 3 ml 0.05 mol/l potassium phosphate buffer, pH 7.65. For preparation for subsequent Phenyl-Sepharose high performance chromatography, the extract was dialyzed using 0.05 mol/l potassium phosphate buffer, pH7.0, having 1.7 mol/l $(NH_4)_2SO_4$.

Step 3: Phenyl Sepharose High Performance Chromatography

The dialyzed enzyme was then subject to chromatography using Phenyl-Sepharose high performance columns, which were equilibrated with a solution of 0.05 mol/l potassium phosphate, pH 7/1.7 mol/l $(NH_4)_2SO_4$. The bound enzyme was eluted using descending linear salt gradients of 100 to 0% $(NH_4)_2SO_4$. 2.75 ml fractions were collected at a flow rate of 1 ml/min. Enzymatic activity eluted at 0.85 mol/l $(NH_4)_2SO_4$ for a total volume of 55 ml.

These samples were dialyzed using several rounds of fresh buffer (0.05 mol/l potassium phosphate, pH 7.65/glycerine, 1:2 v/v) at 4° C. until ammonia could no longer be detected.

Step 4: DEAE CL6B Chromatography

The dialyzed enzyme collected from the preceding purification step was then subject to further chromatography using a DEAE CL6B-column (1×10 cm) with ascending linear gradients of 0.015 mol/l to 1 mol/l KCl in a buffer solution containing 0.05 mol/l potassium phosphate, pH 7.65. The enzyme was eluted using 0.44 mol/l KCl in a volume of 4.5 ml. This fraction was then subject to the dialysis technique as described step 3. The purification protocol is further described in Table 2.

The purified enzyme remained stable in the dialysis buffer for several months, experiencing a loss of activity of 9.1%. The optimal pH value for the purified enzyme, when suspended in phosphate and TEA buffers, was within the range of 8.5–8.75, with maximum activity measured at 47° C.

TABLE 2

Purification of the recombinant creatinine deiminase.

| Purification Stage | Volume (ml) | Activity* (U/ml) | Protein (mg/ml) | Spec. Activity (U/mg) |
|---|---|---|---|---|
| 1) Raw extract | 14.7 | 265 | 26 | 10.2 |
| 2) Ammonium sulphate, 65% supernatant | 23 | 2.2 | 6.7 | 0.33 |
| 3) Ammonium sulphate, 65% resuspended pellet | 3 | 981 | 1.81 | 542 |
| 4) Phenyl-Sepharose HP | 7.2 | 195 | 0.19 | 1026 |
| 5) DEAE-Sepharose CL6B | 1.5 | 569 | 0.4 | 1423 |

*In the presence of ammonium sulphate (steps 1–4), the enzyme activity was determined using the Jaffé method; in step 5, using the coupled optical test.

Example 4

Characterization of the Purified Recombinant Creatinine Deiminase

Homogeneity and Molecular Mass

Figure 9:
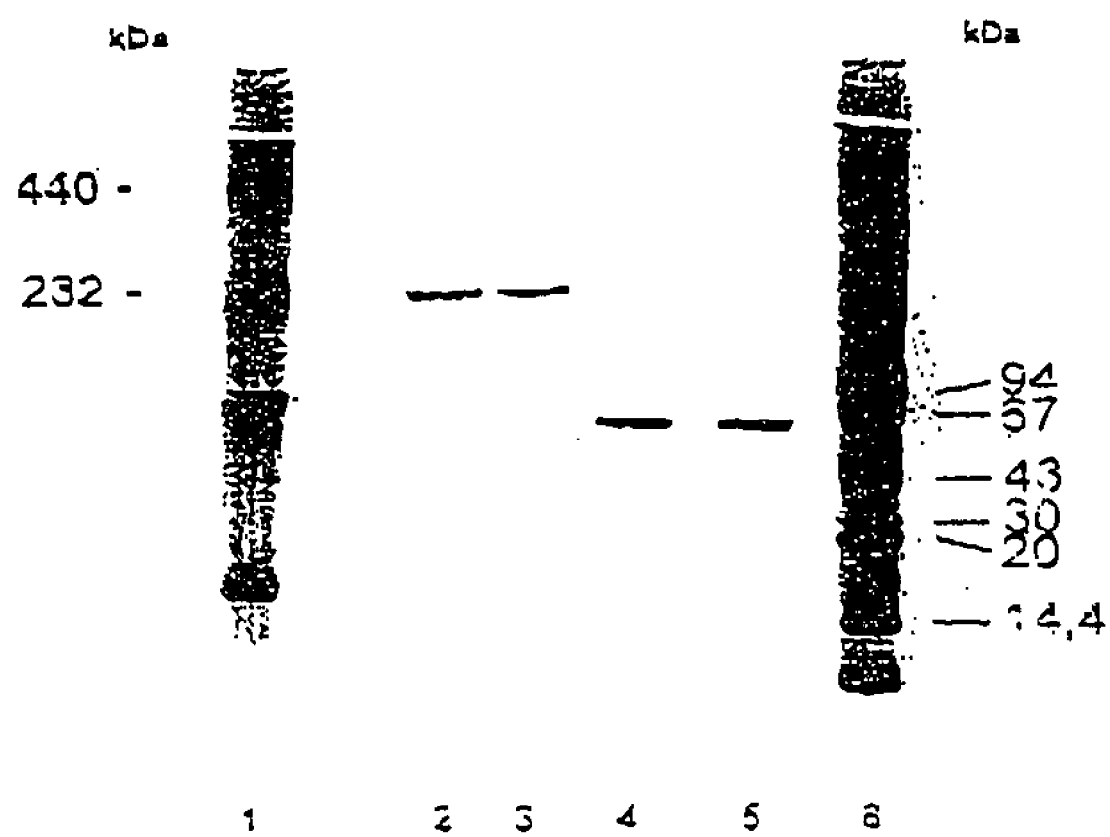
FIG. 9: Analysis of the purified and expressed recombinant creatinine deiminase from T. creatinini. Performed using via PhastGel electrophoresis with polyacrylamide gradients from 8–25%. Lane 1, 6: protein standard; Lane 2, 3: native purified enzyme; Lane 4, 5: purified creatinine deiminase (1 µg), under SDS denaturing conditions.

The purified recombinant enzyme migrated as a single band in native PhastGel gradients (8–25%) between the reference proteins ferritin (440 kDa) and catalase (232 kDa). This showed the homogeneity of the purified creatinine deiminase according to the criteria of native PhastGel gradients. The relative molecular mass of the enzyme was calculated to be 296 kDa by extrapolation to the calibration standard (FIG. 9, lanes 2 and 3). To determine the size of the creatinine deiminase polypeptide, a SDS PhastGel gradient electrophoresis (10–15%) was carried out using a purified enzyme preparation. The electrophoretic mobility of the band corresponded to a relative molecular mass of 49 kDa (FIG. 9, lanes 4 and 5) and was comparable with the value of 45.7 kDa, which was computed according to the derived amino acid sequence of the cdi gene.

Figure 10:
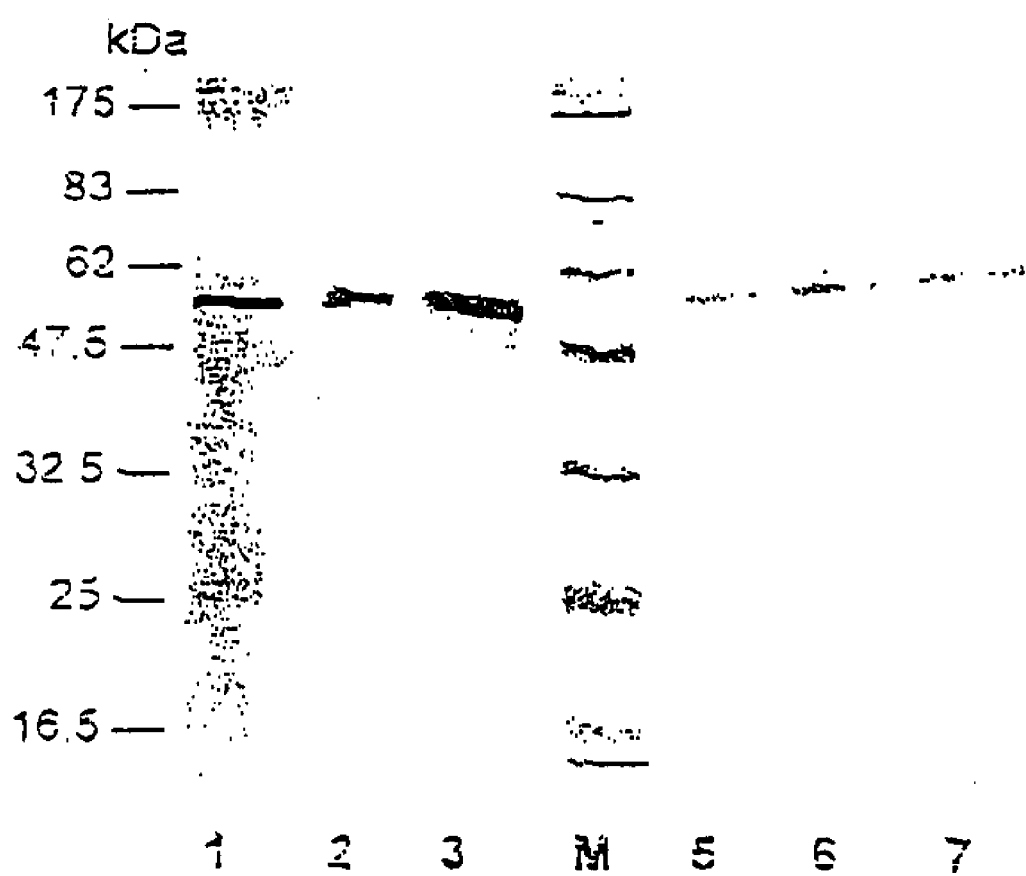
FIG. 10: Western blot analysis of the purified and expressed recombinant creatinine deiminase from T. creatinini. Purified creatinine deiminase from T. creatinini and total cell extract of T. creatinini were subject to gel electrophoresis (12.8% PAGE) under denaturing conditions. The proteins were isolated on a nitrocellulose membrane following transfer. The creatinine deiminase was immunologically identified upon binding a polyclonal antibody. Lanes 1–3: recombinant, purified enzyme; Lanes 5–7: cell extract from T. creatinini.

After separating the recombinant and the native enzyme using SDS/polyacrylamide (12%) gel electrophoresis, Western blotting revealed that the antibodies raised against the recombinant enzyme reacted against both the recombinant and native forms of the enzyme derived from Tissierilla creatinini (FIG. 10, lanes 5–7, and/or lanes 1–3).

Figure 11:
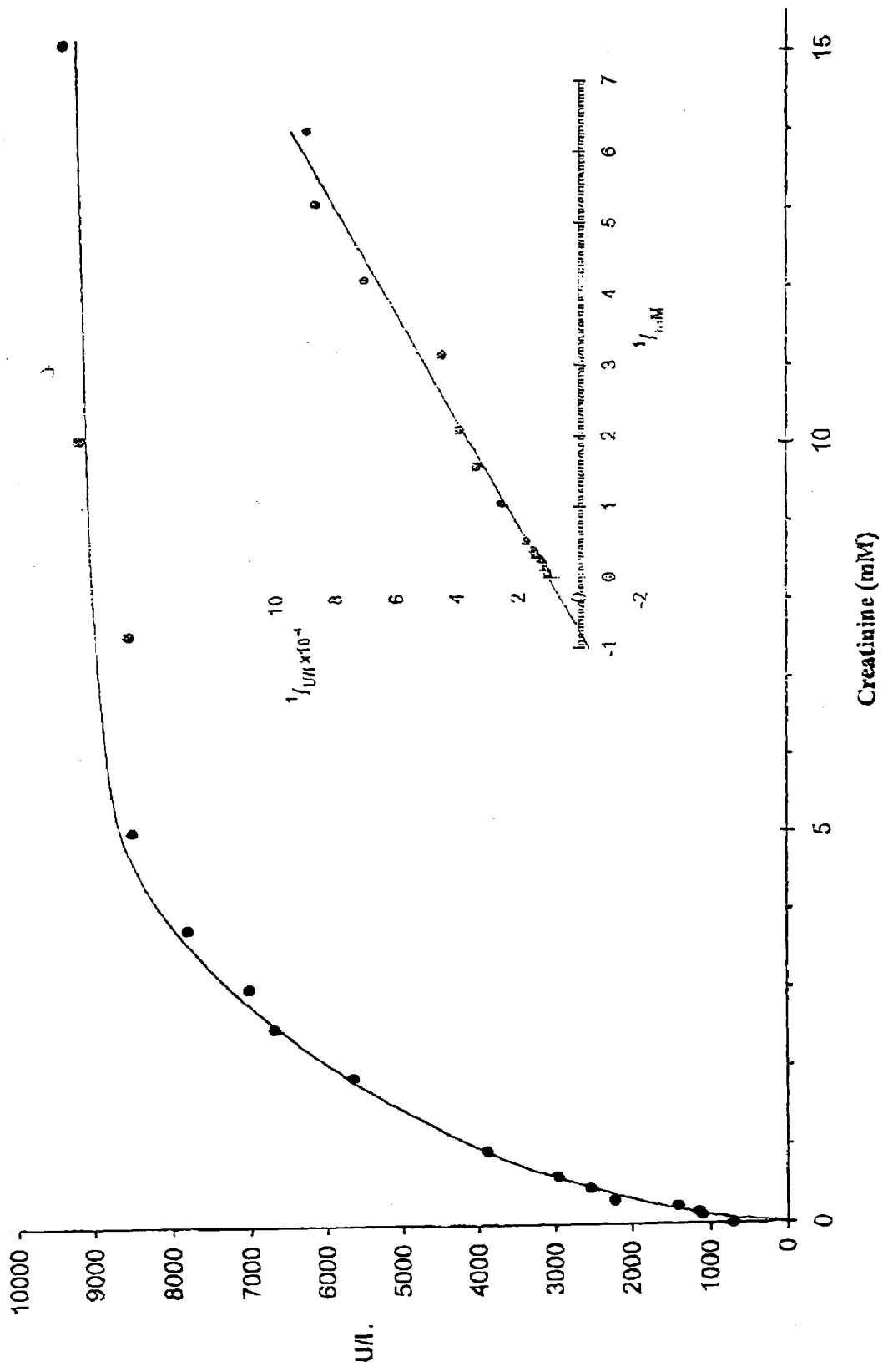
FIG. 11: Enzyme kinetics for the purified and expressed creatinine deiminase from T. creatinini. The enzyme activity as a function of creatinine concentration (0.06 µg purified enzyme sample). Insert: double-reciprocal representation of the Lineweaver Burk plot.

Catalytic Characteristics and Metal Concentration of the Recombinant Creatinine Deiminase Prepared from E. coli The substrate saturation curve for the purified creatinine deiminase is shown in FIG. 11. The $K_m$ value for creatinine was calculated to be 1.1 mmol/l based on a Lineweaver Burke plot analysis; the $V_{max}$ for this enzyme preparation was calculated to be 8.8 U/ml (protein concentration: 61 g/ml, or 1467 U/mg).

A metal analysis of the purified recombinant creatinine deiminase was calculated to be 1.8 zinc atoms per 47.5 kDa subunit.

Example 5

Enzymatic Assay for the Regulation of Creatinine

The activity of the purified recombinant enzyme was determined using a modified enzymatic method developed by Bergmeyer (Bergmeyer, H. U. (1985), Methods of enzymatic analysis 8: 488–507). This method includes the measuring of free ammonia produced during a creatinine deiminase reaction via a coupled optical test, by measuring the volume of NADH consumed by the free ammonia at 340 mm and/or 365 nm. The initial reaction comprised the following concentrations in a final volume of 0.6 ml: TEA buffer 0.11 mol/l, pH 8.6; creatinine 1.5 mmol/l; ADP 1.11 mmol/l; DTE 1 mmol/l; NADH 0.11 mmol/l; 2-oxoglutarate 11 mmol/l; glutamate dehydrogenase 8 U/ml. After incubating the reaction components (5 min at 37° C.), 0.01 ml of the purified recombinant enzyme was transferred to a cuvette and placed into a photometer for observing the extinction acceptance reaction at 340 nm. One enzyme unit was determined to catalyze the degrading of 1 μmol creatinine/min at 37° C.

Example 6

Determining Creatinine Concentration in the Plasma, Serum and Urine

Creatinine concentration was determined using methods as described in Example 5. The control sample contained all of the aforementioned reagents except for the enzyme. The creatinine concentration was calculated using the following formula:

$$C_{Creatinine} = \frac{\Delta E \times Mw \times V}{\varepsilon_{340} \times D \times v \times 10}$$

V=final volume (ml); v=sample volume (ml); Mw=molecular weight, creatinine; $\varepsilon_{340}$=specific micromolecular extinction coefficient of NADH (6.3 cm²/μmol); D=optical path (cm).

A series of interference studies was performed using the purified and expressed creatinine deiminase polypeptide in the presence of the different serum compounds. The compound was provided to the standard reaction mixture and the creatinine deiminase activity was determined using the methods described above. Table 1 lists the compounds tested, which did not show effective interference with creatinine deiminase activity at the indicated concentrations. The recombinant creatinine deiminase showed significant substrate specificity in the presence of the compounds shown in Table 1.

Example 7

Use of the Inventive Method

Figure 3:
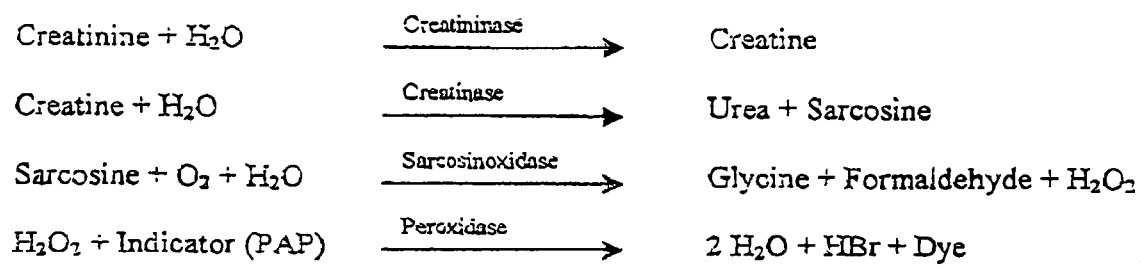
FIG. 3: Enzymatic regulation of creatinine with creatininase, creatinase, sarcosinoxidase and peroxidase. Creatinine is degraded via creatininase, creatinase and sarcosinoxidase to form glycine, formaldehyde and $H_2O_2$. In a subsequent indicator reaction, an increase in $H_2O_2$ is measured via an extinction increase at 510 or 546 nm.
Figure 4:
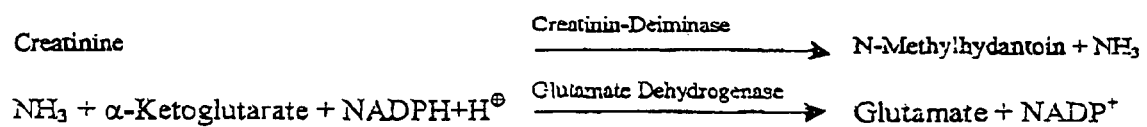
FIG. 4: Enzymatic regulation of creatinine with creatinine deiminase and glutamate dehydrogenase. Creatinine is catalyzed by creatinine deiminase to form n-methylhydantoin and ammonia. Ammonia, in the presence α-ketoglutarate and NADH, is converted to glutamate by glutamate dehydrogenase. The NADH consumption is photometrically measured via the extinction acceptance reaction at 340 and/or 365 nm.
Figure 12:
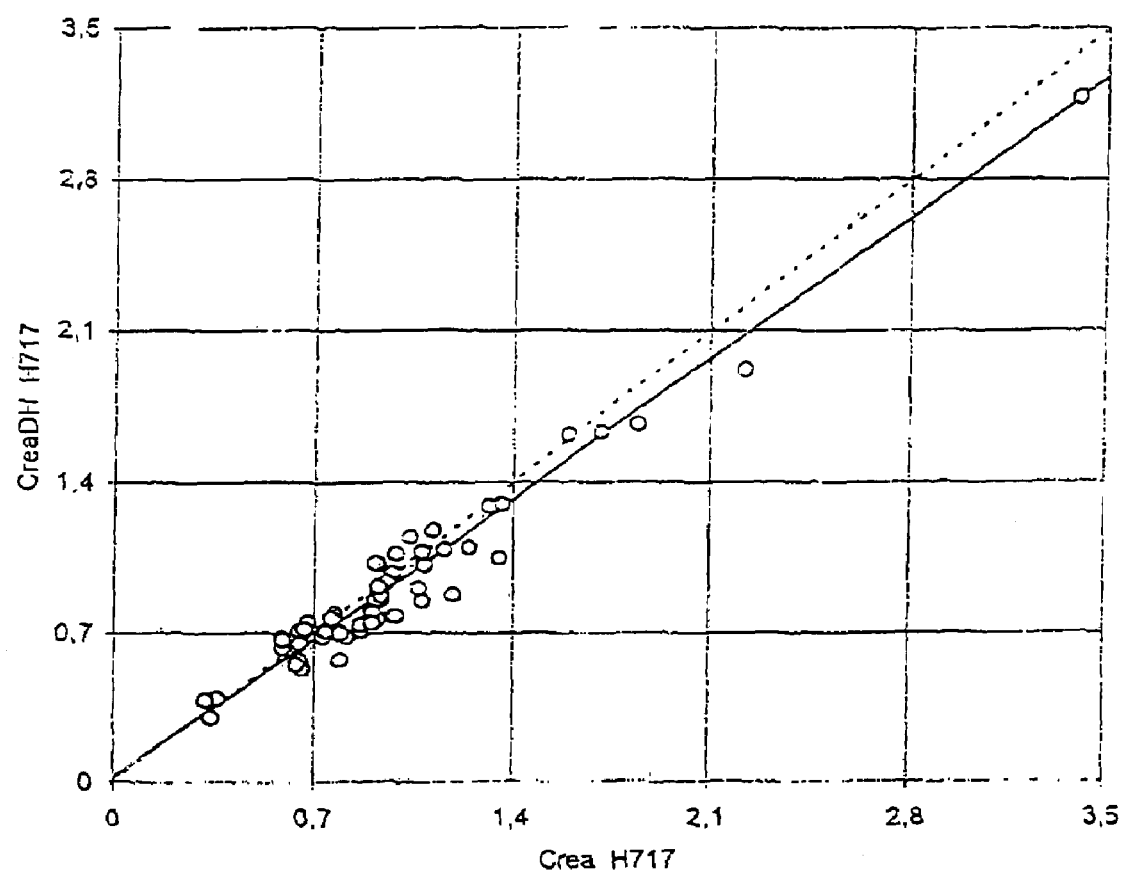
FIG. 12: Determination of creatinine concentration using creatinine deiminase derived from T. creatinini via the coupled optical test using a Hitachi 717 analyzer. The present method is compared to the creatinine determination procedure available from Roche diagnostics (see FIG. 3). The Hitachi 717 analyzer was calibrated using available standards. x axis: Enzymatic creatinine regulation using the Roche diagnostics kit; y axis: Coupled optical test using creatinine deiminase.

The above described procedures for determining creatinine concentration using the optical test protocol were compared with creatinine values determined using known methods available from Roche Diagnostics (see FIG. 3). For this comparison, both methods were carried out using a Hitachi 717 Apparatus, which was calibrated using known standards. The results of this comparison, as depicted in FIG. 12, shows that the coupled optical test is sufficient for use during routine investigation (i.e. reliable reproduction and consistency when compared to the Roche methodology) using the creatinine deiminase polypeptides provided by the present invention.

Those skilled in the art will recognize, or be able to ascertain using no more than routine experimentation, many equivalents of the specific embodiments of the invention described herein. Such equivalents are intended to be encompassed by the following claims.

---

We claim:

1. An isolated or purified nucleic acid coding for a polypeptide having creatinine deiminase activity, selected from the group consisting of:
   (a) the nucleic acid with a sequence as shown in SEQ ID NO: 1 or a fragment thereof coding for a polypeptide having creatinine deiminase activity;
   (b) a nucleic acid having a sequence that is at least 95% identical to (a) and coding for a polypeptide having creatinine deiminase activity; and
   (c) a nucleic acid having a degenerate form of the nucleic acid sequence according to (a) or (b).

2. The nucleic acid of claim 1, wherein the polypeptide having creatinine deiminase activity does not deaminate cytosine.

3. The nucleic acid of claim 1, wherein the nucleic acid is derived from *Tissierella creatinini*.

4. A nucleic acid wherein the nucleic acid sequence is completely complementary to the full length sequence of the nucleic acid of claim 1.

5. The nucleic acid according to claim 1, wherein the nucleic acid comprises DNA or RNA.

6. A recombinant molecule, comprising a nucleic acid sequence according to claim 1.

7. The recombinant molecule according to claim 6, wherein the recombinant molecule is a vector or a plasmid.

8. The recombinant molecule according to claim 7, wherein the vector is a viral vector or a bacteriophage.

9. The recombinant molecule according to claim 6, further comprising an expression control sequence controlling the expression of the nucleic acid molecule.

10. The recombinant molecule according to claim 9, wherein the expression control sequence is homologous or heterologous to the nucleic acid molecule.

11. The recombinant molecule according to claim 9, wherein the expression control sequence comprises a promoter.

12. The recombinant molecule according to claim 9, wherein the expression of the recombinant molecule is controllable.

13. An isolated host cell comprising the molecule according to claim 6.

14. The host cell of claim 13, wherein the cell is selected from the group consisting of a prokaryotic cell, a yeast cell, an insect cell, a plant cell and a mammalian cell.

15. The host cell according to claim 14, wherein the prokaryotic cell is selected from the group consisting of *Escherichia coli* and *Bacillus subtilis*.

16. The host cell of claim 13, wherein the nucleic acid molecule is expressed in the host cell to produce a polypeptide.

17. The host cell according to claim 16, wherein the polypeptide is secreted.

18. A method for preparing a polypeptide having a creatinine deiminase activity, said method comprising expressing in a host cell, a nucleic acid according to claim 1 and isolating the polypeptide from the host cell.

19. The method according to claim 18, wherein isolating the polypeptide further comprises precipitating the polypeptide via ammonium sulphate and subjecting the polypeptide to chromatography using a sepharose containing column.

20. A kit for determining creatinine concentration in a sample, said kit comprising:
    (a) a nucleic acid sequence of claim 1 or a host cell of claim 13; and
    (b) a reagent for determining the amount of ammonia formed in the sample.

* * * * *

SEQUENCE LISTING

```
<160> NUMBER OF SEQ ID NOS: 2

<210> SEQ ID NO 1
<211> LENGTH: 1593
<212> TYPE: DNA
<213> ORGANISM: Tissierella creatinini

<400> SEQUENCE: 1
ctggcattag tgttattggc tatagcaaca attttgtcaa taactgataa aaatacatta      60
acaaaagaaa aactgtaagc tattaacaat gctaaatttt taaggagtga ttttatgatg     120
aaaaagttta ttaatgcaaa gatttacaag aacaatgaag caacagaaat tttagtagaa     180
gacggtaaaa tcaaagagat tggtaataac ttagcagact gtaaagaagt aattgatcta     240
ggcggtaaaa tggttactcc accttatgta gatcctcacc tacatttaga ttatgtgtat     300
acattggctg aacttggaaa aactggtgct ggctcaggaa ctcttttga agctattgaa     360
```

```
atgtggccag tatttaaaaa gactttaact gtagaaagcg ttaaaaaact tgctcttaag    420
ggggttatgg atgaggtttc ccaaggggta caacatattc gtacacatat agatgtaact    480
gatccaaaat tcacaggtct aaaagctatg ttggaaatga agaagaatt aaaggacata     540
gttgatatcc aaatagtatc attcccacaa caaggaatgt acacatataa gggtggacgt    600
gaattagtag aagaagcact taagatgggt gcagatgttg ttggaggaat tccgcattat    660
gaaccagcta gagaatatgg tgaaatgtct gttaaagcca cagttgaact tgctatgaaa    720
tatgataagc taatagatgt tcactgtgat gagacagatg atcctcaagc acgttttatt    780
gagctattaa atgcacttgt ttatttggaa ggttatggtg caaaaacttc agctagccat    840
acttgttcat ttggttcagc agatgattca tatgcatata gaatgataga cttattcaaa    900
aagagcaaga taaacttcat ctctaatcca actgaaaatg cgtatctaca aggccgtcat    960
gacacttatc caaagcgtcg tggattgact agagttaaag aatttatgga gcatggtatt   1020
aatgttgcat ttgcacaaga ttcaataaac gatccatggt atccaatggg taacggaaat   1080
atgatgaata tacttgacaa tggaattcat ttagctcaaa taatgtcacc acaagatata   1140
gaaaaagatt tagatttaat tacctacaat ggtgctcgtt gcctaaatat ccaagataaa   1200
tatttattag aagtaggtaa agattcaaac tttatcgttc ttaacggaga cagcccattc   1260
gatgtaataa gaaccgtgc taatgttctt gcttgtgtta gaaaggaga attctattta     1320
agcaaaaacc agtagaatat gatgtaaaac ttgatttagg cgtaaaatat aatatttta    1380
aaataaattc caaattaacc ccccggtggt gtaataaact ccatcggggg gttttttgtg   1440
ttccagtaga aaataaaaaa atgatataaa aatttagtag tttgaaaaac ttaaataaag   1500
aaagggcgga tttagaatga gtcaaagaga cgtattatat tcaccagatg caaagtacaa   1560
agataataag ggtaaatatg gaattgattt agg                                1593
```

<210> SEQ ID NO 2
<211> LENGTH: 406
<212> TYPE: PRT
<213> ORGANISM: Tissierella creatinini

<400> SEQUENCE: 2

```
Met Met Lys Lys Phe Ile Asn Ala Lys Ile Tyr Lys Asn Asn Glu Ala
 1               5                  10                  15

Thr Glu Ile Leu Val Glu Asp Gly Lys Ile Lys Glu Ile Gly Asn Asn
                20                  25                  30

Leu Ala Asp Cys Lys Glu Val Ile Asp Leu Gly Gly Lys Met Val Thr
            35                  40                  45

Pro Pro Tyr Val Asp Pro His Leu His Leu Asp Tyr Val Tyr Thr Leu
        50                  55                  60

Ala Glu Leu Gly Lys Thr Gly Ala Gly Ser Gly Thr Leu Phe Glu Ala
65                  70                  75                  80

Ile Glu Met Trp Pro Val Phe Lys Lys Thr Leu Thr Val Glu Ser Val
                85                  90                  95

Lys Lys Leu Ala Leu Lys Gly Val Met Asp Glu Val Ser Gln Gly Val
            100                 105                 110

Gln His Ile Arg Thr His Ile Asp Val Thr Asp Pro Lys Phe Thr Gly
        115                 120                 125

Leu Lys Ala Met Leu Glu Met Lys Glu Glu Leu Lys Asp Ile Val Asp
    130                 135                 140

Ile Gln Ile Val Ser Phe Pro Gln Gln Gly Met Tyr Thr Tyr Lys Gly
145                 150                 155                 160
```

-continued

```
Gly Arg Glu Leu Val Glu Glu Ala Leu Lys Met Gly Ala Asp Val Val
                165                 170                 175

Gly Gly Ile Pro His Tyr Glu Pro Ala Arg Glu Tyr Gly Glu Met Ser
                180                 185                 190

Val Lys Ala Thr Val Glu Leu Ala Met Lys Tyr Asp Lys Leu Ile Asp
            195                 200                 205

Val His Cys Asp Glu Thr Asp Asp Pro Gln Ala Arg Phe Ile Glu Leu
        210                 215                 220

Leu Asn Ala Leu Val Tyr Leu Glu Gly Tyr Gly Ala Lys Thr Ser Ala
225                 230                 235                 240

Ser His Thr Cys Ser Phe Gly Ser Ala Asp Asp Ser Tyr Ala Tyr Arg
                245                 250                 255

Met Ile Asp Leu Phe Lys Lys Ser Lys Ile Asn Phe Ile Ser Asn Pro
                260                 265                 270

Thr Glu Asn Ala Tyr Leu Gln Gly Arg His Asp Thr Tyr Pro Lys Arg
                275                 280                 285

Arg Gly Leu Thr Arg Val Lys Glu Phe Met Glu His Gly Ile Asn Val
        290                 295                 300

Ala Phe Ala Gln Asp Ser Ile Asn Asp Pro Trp Tyr Pro Met Gly Asn
305                 310                 315                 320

Gly Asn Met Met Asn Ile Leu Asp Asn Gly Ile His Leu Ala Gln Ile
                325                 330                 335

Met Ser Pro Gln Asp Ile Glu Lys Asp Leu Asp Leu Ile Thr Tyr Asn
                340                 345                 350

Gly Ala Arg Cys Leu Asn Ile Gln Asp Lys Tyr Leu Leu Glu Val Gly
                355                 360                 365

Lys Asp Ser Asn Phe Ile Val Leu Asn Gly Asp Ser Pro Phe Asp Val
                370                 375                 380

Ile Arg Asn Arg Ala Asn Val Leu Ala Cys Val Arg Lys Gly Glu Phe
385                 390                 395                 400

Tyr Leu Ser Lys Asn Gln
                405
```